(12) United States Patent
Yang

(10) Patent No.: US 9,387,037 B2
(45) Date of Patent: Jul. 12, 2016

(54) ELECTROSURGICAL GENERATOR

(75) Inventor: Teo Heng Jimmy Yang, Cardiff (GB)

(73) Assignee: GYRUS MEDICAL LIMITED, Cardiff (GB)

(*) Notice: Subject to any disclaimer, the term of this patent is extended or adjusted under 35 U.S.C. 154(b) by 345 days.

(21) Appl. No.: 14/110,226

(22) PCT Filed: Apr. 4, 2012

(86) PCT No.: PCT/GB2012/000312
§ 371 (c)(1),
(2), (4) Date: Nov. 1, 2013

(87) PCT Pub. No.: WO2012/136956
PCT Pub. Date: Oct. 11, 2012

(65) Prior Publication Data
US 2014/0058382 A1 Feb. 27, 2014

(30) Foreign Application Priority Data
Apr. 7, 2011 (GB) .................................. 1105876.5

(51) Int. Cl.
*A61B 18/18* (2006.01)
*A61B 18/12* (2006.01)
(Continued)

(52) U.S. Cl.
CPC ............. *A61B 18/18* (2013.01); *A61B 18/1206* (2013.01); *A61B 18/1445* (2013.01); *A61B 2018/0063* (2013.01);
(Continued)

(58) Field of Classification Search
CPC ........... A61B 18/1206; A61B 18/1445; A61B 2018/124; A61B 2018/00601; A61B 2018/0063; A61B 2018/00607
See application file for complete search history.

(56) References Cited

U.S. PATENT DOCUMENTS

| 5,919,189 A | 7/1999 | Benderev |
| 6,174,309 B1 | 1/2001 | Wrublewski et al. |
| 6,293,942 B1 | 9/2001 | Goble et al. |

(Continued)

FOREIGN PATENT DOCUMENTS

| CN | 101072543 A | 11/2007 |
| EP | 0 754 437 A2 | 1/1997 |
| WO | WO 2010/108523 A1 | 9/2010 |

OTHER PUBLICATIONS

International Search Report issued in International Application No. PCT/GB2012/000312 mailed Jul. 24, 2012.

(Continued)

*Primary Examiner* — Michael Peffley
(74) *Attorney, Agent, or Firm* — Oliff PLC

(57) ABSTRACT

An electrosurgical generator for generating radio frequency power, includes a radio frequency output stage having three or more output connections, and one or more sources of radio frequency output power coupled to the output stage. A controller causes the system to supply a first coagulating RF waveform to the output connections or a second cutting RF waveform to the output connections. The first RF waveform is delivered between a first pair of the output connections, and the second RF waveform is delivered between a second pair of the output connections. In a first mode of operation the controller supplies the first coagulating RF waveform, and in a second subsequent mode of operation the controller supplies the second cutting RF waveform for a first predetermined period of time followed by the first coagulating RF waveform for a second predetermined period of time, both periods being in excess of 1 second.

5 Claims, 7 Drawing Sheets

(51) Int. Cl.
*A61B 18/14* (2006.01)
*A61B 18/00* (2006.01)

(52) U.S. Cl.
CPC ............. *A61B 2018/00589* (2013.01); *A61B 2018/00601* (2013.01); *A61B 2018/124* (2013.01)

(56) References Cited

U.S. PATENT DOCUMENTS

| | | | |
|---|---|---|---|
| 6,626,901 B1 * | 9/2003 | Treat | A61B 18/085 606/29 |
| 6,966,907 B2 * | 11/2005 | Goble | A61B 18/12 606/37 |
| 7,204,835 B2 | 4/2007 | Latterell et al. | |
| 7,344,532 B2 | 3/2008 | Goble et al. | |
| 2005/0113820 A1 * | 5/2005 | Goble | A61B 18/1206 606/34 |
| 2008/0009850 A1 | 1/2008 | Goble et al. | |
| 2009/0234355 A1 | 9/2009 | Edwards et al. | |

OTHER PUBLICATIONS

Written Opinion of the International Searching Authority issued in International Application No. PCT/GB2012/000312 mailed Jul. 24, 2012.

May 27, 2015 Office Action issued in Chinese Patent Application No. 201280017456.8.

Aug. 4, 2011 Search Report issued in British Patent Application No. GB1105876.5.

\* cited by examiner

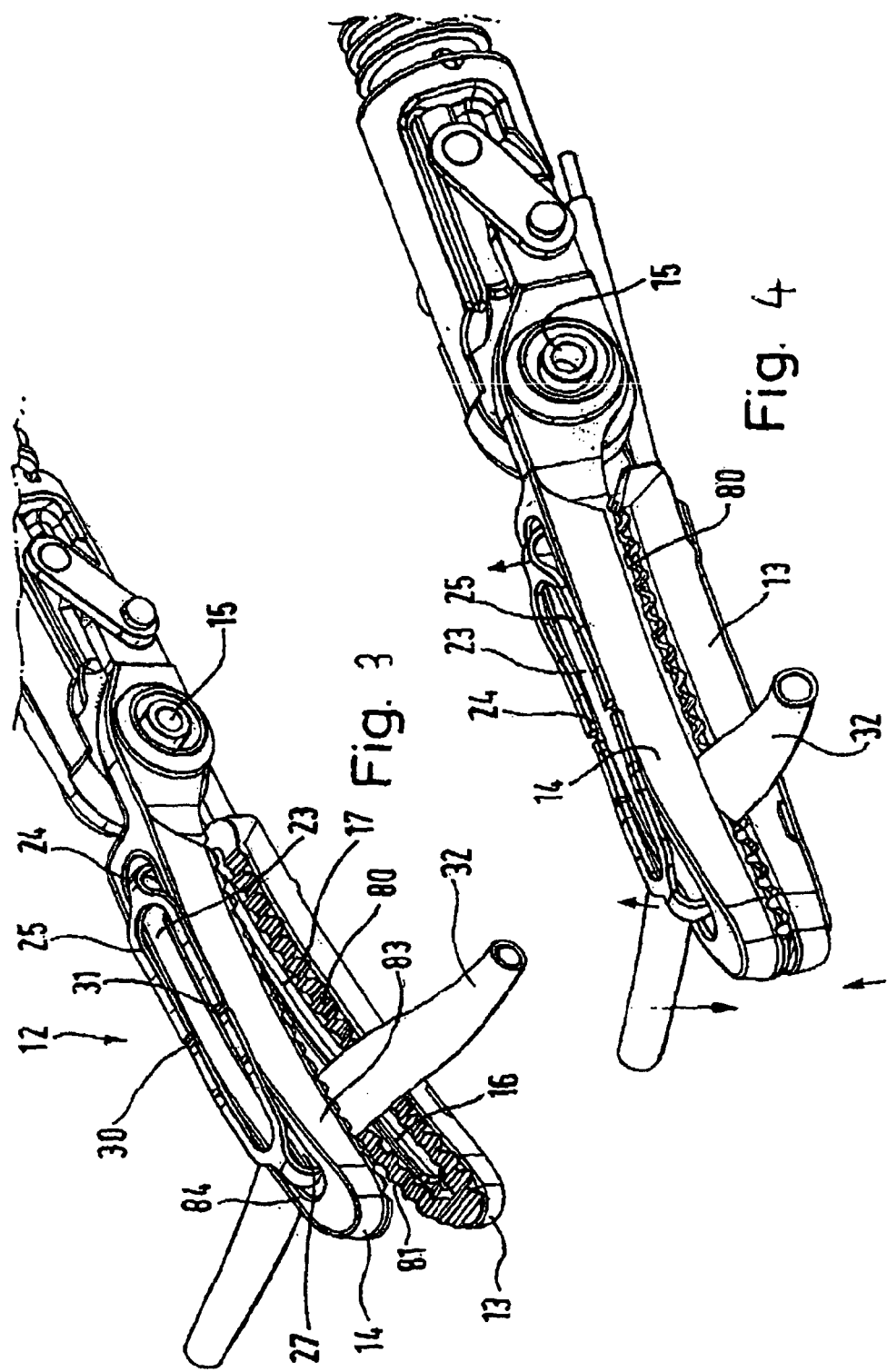

ELECTROSURGICAL GENERATOR

TECHNICAL FIELD

This invention relates to an electrosurgical generator suitable for use in an electrosurgical system for the treatment of tissue. Such systems are commonly used for the vaporisation and/or coagulation of tissue in surgical intervention, most commonly in "keyhole" or minimally invasive surgery, and also in "open" surgery. The invention further relates to an electrosurgical system, and a method of cutting and sealing tissue.

BACKGROUND TO THE INVENTION AND PRIOR ART

It is known to provide an electrosurgical instrument in which the cutting of tissue is carried out by means of an elongate electrosurgical electrode extending along the inner surface of one of a pair of jaw elements. U.S. Pat. Nos. 6,174,309 & 7,204,835 are two examples of this kind of instrument. In this instrument, it is usual to grasp tissue between the jaws, perform an electrosurgical tissue coagulating action on the tissue grasped between the jaws, and finally perform an electrosurgical cut on the coagulated tissue. The present invention attempts to provide an improvement to this type of procedure.

SUMMARY OF INVENTION

Accordingly, an electrosurgical generator is provided for generating radio frequency power, the generator comprising:
  (i) a radio frequency output stage having three or more output connections,
  (ii) one or more sources of radio frequency output power coupled to the output stage,
  (iii) a controller operable to cause the system to supply a first coagulating RF waveform to the output connections or a second cutting RF waveform to the output connections, the controller including means for feeding the waveforms to the output connections such that the first RF waveform is delivered between a first pair of the output connections, and the second RF waveform is delivered between a second pair of the output connections,
  the arrangement of the system being such that in a first mode of operation the controller supplies the first coagulating RF waveform, and in a second subsequent mode of operation the controller supplies the second cutting RF waveform for a first predetermined period of time followed by the first coagulating RF waveform for a second predetermined period of time, the first and second predetermined period of time both being in excess of 1.5 seconds.

Typically, the user of the electrosurgical generator will instigate the first mode of operation by activating the blue pedal on a footswitch connected to the electrosurgical generator. This is the conventional pedal for supplying a coagulation signal from the generator. The second subsequent mode of operation is typically instigated by the user of the electrosurgical generator activating the yellow pedal on the footswitch. This is the conventional pedal for supply of a cutting signal from the generator, but in this case, the activation of the yellow pedal causes the generator to supply a cutting RF waveform followed by a further burst of RF coagulating waveform.

Typically, the first predetermined period of time, during which the controller supplies the cutting RF waveform, is in the range of 1.5 to 5 seconds, and preferably 1.5 to 3 seconds.

Conveniently, the second predetermined period of time, during which the controller supplies the coagulating RF waveform, is in the range of 1.5 to 6 seconds, and preferably 1.5 to 3 seconds.

Preferably, in the first mode of operation, the controller supplies the first coagulating RF waveform for an initial predetermined period of time, typically in the range of 1.5 to 4 seconds. It should be understood that this initial period of time may be insufficient for the complete coagulation of the tissue to occur, unlike in conventional systems, where the electrosurgical generator attempts to coagulate the tissue completely before the electrosurgical cut is performed. In conventional systems, the electrosurgical generator completely coagulates the tissue before the tissue is cut, in order to ensure that there is no bleeding once the tissue is severed. However, this means that the electrosurgical cut is being performed on completely coagulated tissue, which may affect the effectiveness of the electrosurgical cut. RF energy requires some degree of moisture to be present within the tissue in order to be effective. If the tissue is coagulated to the extent that it has become desiccated and relatively free of moisture, the electrosurgical cut will require a relatively long period of application in order to be effective, or may even be ineffective due to the dryness of the tissue.

In contrast, the generator of the present invention does not attempt to perform the complete coagulation of the tissue before the electrosurgical cut is undertaken, leaving sufficient moisture within the tissue to ensure that the electrosurgical cut is effective. Any further coagulation required to complete the process is carried out after the electrosurgical cut, in the second predetermined period of time during which the RF coagulating waveform is reapplied.

The second subsequent mode of operation (during which the cutting RF waveform is supplied for the first period of time followed by the coagulating RF waveform supplied for the second period of time) is provided automatically by the electrosurgical generator in response to a single activation, typically by the yellow pedal of the footswitch, or conceivably from a handswitch present on the electrosurgical instrument connected to the generator. This is in contrast to the prior art situation, in which a surgeon, having activated the yellow pedal in order to obtain the RF cutting waveform, notices subsequent bleeding and re-activates the generator using the blue pedal to obtain further tissue coagulation. In the present invention, the generator, in response to a single activation, supplies the cutting RF waveform followed by the RF coagulation waveform, each for a predetermined period of time. This allows for the initial coagulation of the tissue to be shorter, preventing over-coagulation of the tissue prior to cutting, with the resulting difficulties previously described.

The invention further resides in an electrosurgical generator for generating radio frequency power, comprising:
  (i) a radio frequency output stage having three or more output connections,
  (ii) one or more sources of radio frequency output power coupled to the output stage,
  (iii) a controller operable to cause the system to supply a first coagulating RF waveform to the output connections or a second cutting RF waveform to the output connections, the controller including means for feeding the waveforms to the output connections such that the first RF waveform is delivered between a first pair of the output connections, and the second RE waveform is delivered between a second pair of the output connections,
  the arrangement of the system being such that in at least one mode of operation the controller provides a first phase in which the first coagulating waveform is supplied, followed by a second phase in which the second cutting RF waveform is supplied, followed by a third phase in which the first coagulating RF waveform is supplied, the period of application of each of the first, second and third phases being in excess of 1.5 seconds.

In this arrangement, the generator supplies the three phases described above automatically one after the other, in response to a single activation of the generator. This is in contrast to prior art situations, in which the surgeon needs to toggle between the blue and yellow pedals on the footswitch connected to the generator, in order to achieve the desired combination of cutting and coagulating signals. The generator of the present invention supplies a coagulating RF waveform to the tissue, followed automatically by a cutting RF waveform, and followed subsequently by a repeat of the coagulating RF waveform, all for a single activation of the generator.

The invention further resides in an electrosurgical system including an electrosurgical generator for generating radio frequency power, and a bipolar electrosurgical instrument, the instrument comprising:
(a) a body including a handle;
(b) a jaw assembly joined to the body and arranged such that manipulation of the handle allows tissue at a surgical site to be clamped between first and second jaws of the jaw assembly;
the jaw assembly including at least first and second sealing electrodes, and a cutting electrode supported on one of the first and second jaws,
and the generator comprising:
(i) a radio frequency output stage having three or more output connections, a first output connection being connected to the first sealing electrode, the second output connection to the second sealing electrode and the third output connection to the cutting electrode,
(ii) one or more sources of radio frequency output power coupled to the output stage,
(iii) a controller operable to cause the system to supply a first coagulating RF waveform to the output connections or a second cutting RF waveform to the output connections, the controller including means for feeding the waveforms to the output connections such that the first RF waveform is delivered between a first pair of the output connections and hence between the first and second sealing electrodes, and the second RF waveform is delivered between a second pair of the output connections and hence between the cutting electrode and one or both of the sealing electrodes,
the arrangement of the system being such that in at least one mode of operation the controller provides a first phase in which the first coagulating RF waveform is supplied, followed by a second phase in which the second cutting RF waveform is supplied, followed by a third phase in which the first coagulating RF waveform is supplied, the period of application of each of the first second and third phases being in excess of 1.5 seconds.

The above-described jawed instrument, with first and second sealing electrodes and a cutting electrode supported on one of the first and second jaws, is the preferred instrument for use with the electrosurgical generator described previously.

The invention further resides in a method of cutting and sealing tissue comprising the steps of
(i) grasping the tissue with an electrosurgical instrument including a jaw assembly including at least first and second sealing electrodes, and a cutting electrode supported on one of the first and second jaws of the jaw assembly,
(ii) applying a first coagulating RF waveform between the first and second sealing electrodes of the jaw assembly for at least 1.5 seconds,
(iii) continuing to grasp the tissue between the jaws of the jaw assembly,
(iv) applying a second cutting RF waveform between the cutting electrode and one or both of the first and second sealing electrodes for at least 1.5 seconds,
(v) continuing to grasp the tissue between the jaws of the jaw assembly,
(vi) re-applying the first coagulating RF waveform between the first and second sealing electrodes of the jaw assembly for at least 1.5 seconds, and
(vii) releasing the tissue from the jaw assembly.

It should be appreciated that the periods of time for the application of the coagulating RF waveform and the cutting RF waveform are typically at least 1 second, which is significantly greater than the time periods involved in "blended" RF waveforms, such as those discussed in patents such as U.S. Pat. Nos. 6,293,942 or 6,966,907. In these systems, a blended waveform is produced by constantly alternating between cutting and coagulating waveforms many times per second. In the present invention, the generator supplies one type of waveform for a period of at least 1 second, before switching to a subsequent different type of waveform.

A further aspect of the invention provides an electrosurgical generator for generating radio frequency power, comprising:
(i) a radio frequency output stage having a plurality of output connections,
(ii) one or more sources of radio frequency output power coupled to the output stage,
(iii) a controller operable to cause the system to supply a first coagulating RF waveform to the output connections or a second cutting RF waveform to the output connections, the controller including means for feeding the waveforms to the output connections;
the arrangement of the generator being such that in response to an activation signal from a user the controller supplies the second cutting RF waveform for a first period of time required to perform an electrosurgical cut, followed automatically by the first coagulating RF waveform for a second period of time required to complete coagulation of the cut tissue.

In this aspect the activation signal, which may be a cutting activation signal, causes the electrosurgical cutting to be performed in a similar manner to the prior art, but then the cutting signal is followed automatically by a coagulating signal, to complete coagulation of the cut tissue. This automatic coagulation signal allows the tissue not to be coagulated or dessicated fully in advance of the cut, with the attendant advantages noted above.

In this aspect the generator may be further arranged to supply the first coagulating RF waveform for a coagulation time period required to partially coagulate the tissue to be cut prior to the supply of the second cutting RF waveform for the first period of time, the supply of the first coagulating RF waveform for the coagulation time period being in response to the activation signal. Hence, a 3 stage automatic operation can be obtained in response to an activation, where the tissue is first partially coagulated, then cut, and then the coagulation is automatically completed.

In addition, the controller may supply the second cutting RF waveform for the first period of time and the first coagulating RF waveform for the second period of time in order once respectively per activation signal. This provides control over the RF, in that there is a direct correlation between the receipt of an activation signal and the number of cutting and coagulation cycles, being effectively one to one. Such operation differs from the "blended" cutting and coagulation signals of the prior art, where the cutting and coagulation signals are alternated very quickly, and hence several (in fact many) cutting and coagulation cycles can be undertaken for a single activation.

DESCRIPTION OF THE DRAWINGS

Embodiments of the invention will now be further described, by way of example only, with reference to the accompanying drawings, in which:

FIG. 3 is a perspective view of the end effector assembly of the instrument of FIG. 1, shown with the jaws in the open position, FIG. 4 is a perspective view of the end effector assembly of the instrument of FIG. 1, shown with the jaws in the closed position.

DESCRIPTION OF THE EMBODIMENTS

Figure 1:
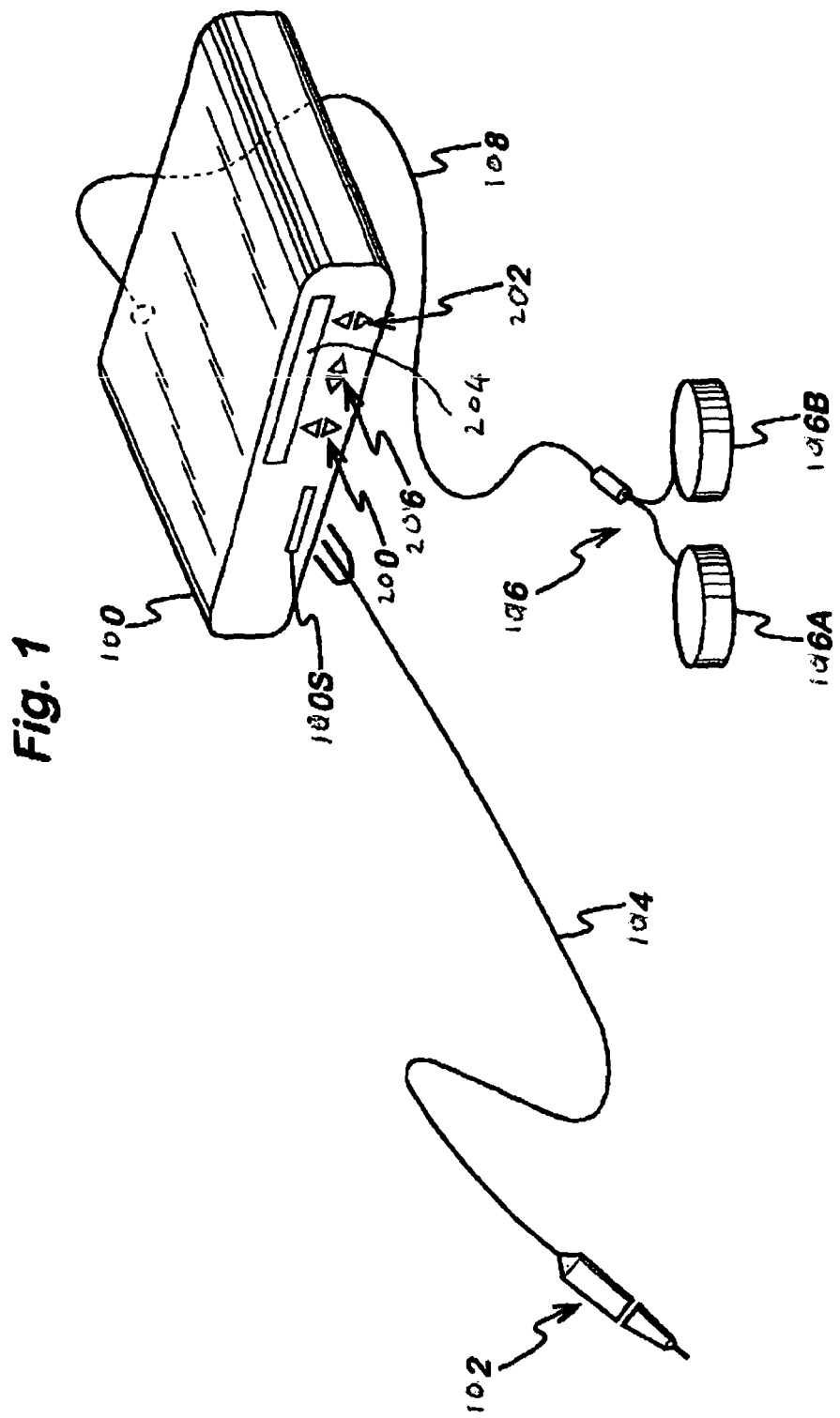
FIG. 1 is a schematic view of a surgical system including a generator in accordance with the invention.

Referring to FIG. 1, a generator 100 has an output socket 1005 providing a radio frequency (RF) output for an instrument 102 via a connection cord 104. Activation of the generator may be performed from the instrument 102 via a connection in cord 104 or by means of a footswitch unit 106, as shown, connected to the rear of the generator by a footswitch connection cord 108. In the illustrated embodiment footswitch unit 106 has two footswitches 106A and 106B for selecting a coagulation mode and a cutting mode of the generator respectively. The generator front panel has push buttons 200 and 202 for respectively setting coagulation and cutting power levels, which are indicated in a display 204. Push buttons 206 are provided as a means for selection between alternative coagulation and cutting waveforms.

Figure 2:
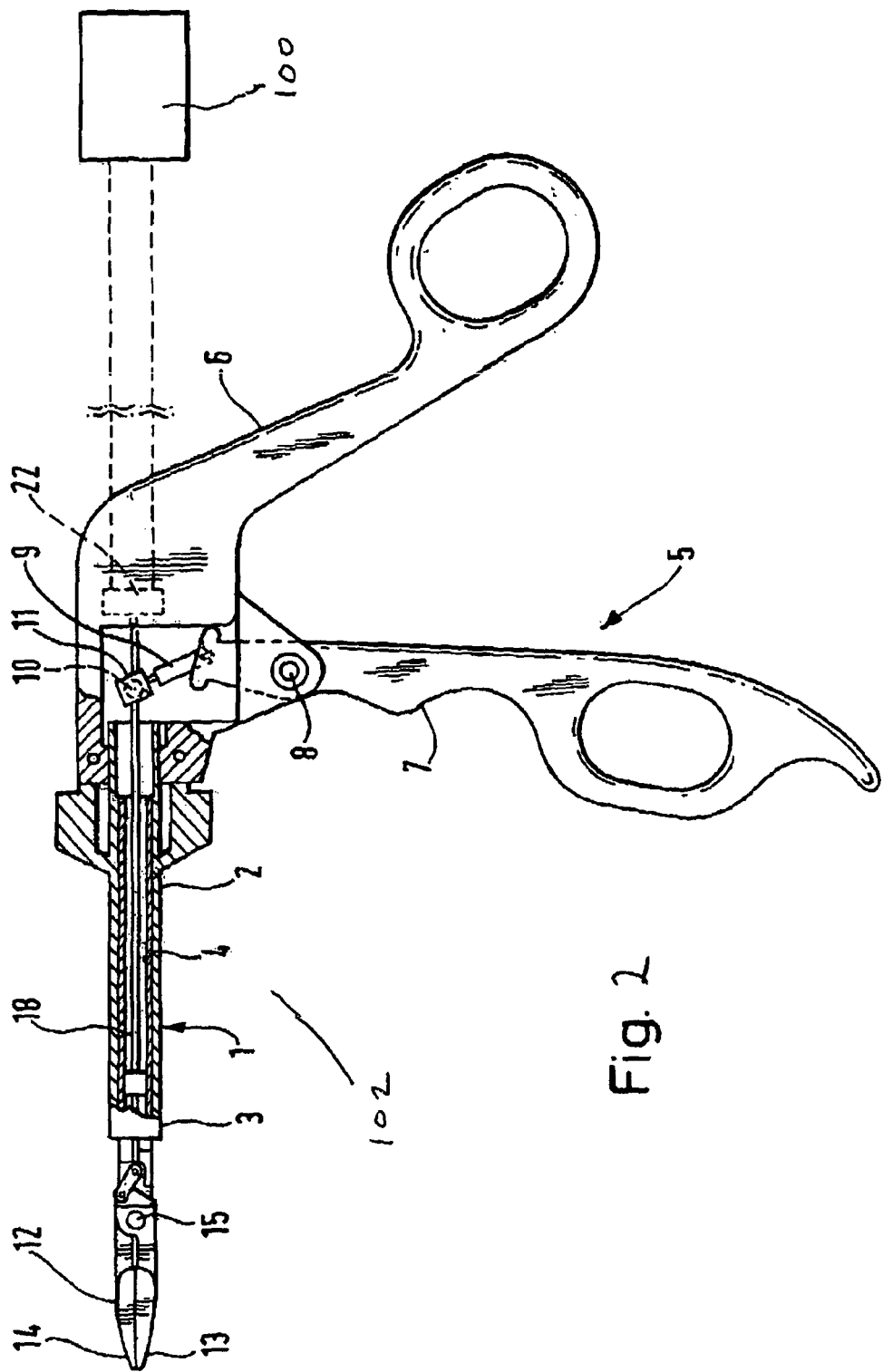
FIG. 2 is a schematic sectional view of a surgical instrument for use with a generator in accordance with the invention.

FIG. 2 shows the instrument 102 connected to the generator 100. Referring to FIG. 2, a bipolar forceps device includes an elongated tubular shaft 1 with a proximal end 2, a distal end 3, and a lumen 4 which extends for the entire length of the tubular member. At the proximal end 2 of the tubular member 1 is a scissors-type handle assembly 5 with a first handle 6 and a second handle 7. The second handle 7 is pivotable with respect to the first handle 6, about a pivot pin 8. In a known design of actuation mechanism, the second handle 7 has a pin 9 affixed to the top thereof, such that movement of that handle causes a corresponding movement to a sphere 10 supported in a U-shaped cradle 11.

Fitted into the distal end 3 of the tubular member 1 is a forceps jaw assembly 12, more particularly shown in FIG. 2. The jaw assembly 12 comprises a first jaw member 13 and a second jaw member 14, pivotally joined to each other by an insulated rivet 15. The jaw member 13 is constituted by two tissue-contacting members 80 & 81, separated by a insulator 17, typically of ceramic or other insulating material. The jaw member 13 is also provided with a relatively-long, but narrow cutting electrode 16 mounted on the insulator 17. The jaw members 13 and 14, together with the cutting electrode 16, are connected to the electrosurgical generator 100 by means of a connector 22, and wires or conductive rods 18 running through the lumen 4 of the tubular member 1.

As shown in FIG. 3, the cutting electrode 16 is in the form of an elongate rail, extending along the length of the jaw member 13. The rail 16 is mounted on top of the ceramic insulator 17 such that it is insulated from the tissue-contacting members 80 & 81 of the conductive jaw member 13. The rail 16 is typically 100 to 200 microns in width, and protrudes from the ceramic insulator 17 by a distance of approximately 50 microns. When the jaw assembly 12 is in its closed position, the rail 16 is received in a corresponding longitudinal recess 23 in the jaw member 14, as will now be described in further detail.

The recess 23 runs completely through the jaw member 14 from top to bottom, creating an opening therein. This recess divides the jaw member 14 into two further tissue-contacting members 82 & 83. Received within the recess 23 is a support member 24 in the form of a sprung frame 25, attached to the top of the jaw member 14 by welding at positions 30 and 31. Depending from the frame 25 is a longitudinally extending anvil 27, formed of an insulating polymer material, and aligned with the cutting electrode 16 in the jaw member 13. When the jaw members 13 and 14 are closed, as shown in FIG. 4, the anvil 27 pushes tissue 32 against the cutting electrode 16.

Figure 5:
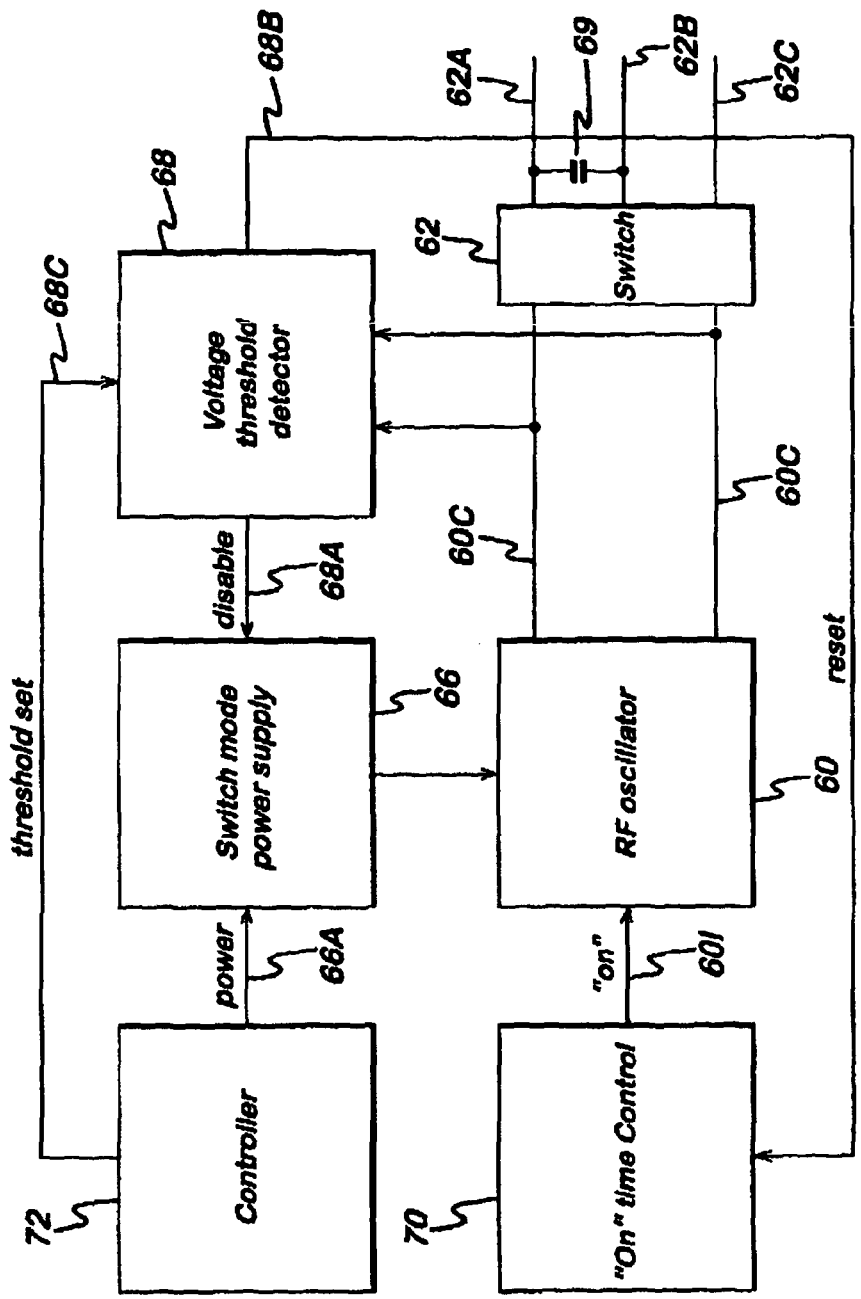
FIG. 5 is a schematic block diagram of the generator of FIG. 1, FIGS. 6A & 6B are schematic diagrams of the switching circuit of FIG. 5, shown in different modes of operation.

Referring to FIG. 5, the generator comprises a radio frequency (RF) output stage in the form of a power oscillator 60 having a pair of output lines 60C for coupling via switching circuit 62 to the instrument 12. Switching circuit 62 has three output connections 62A, 62B and 62C for connection to the electrodes of the instrument as will be described later. Power is supplied to the oscillator 60 by a switched mode power supply 66.

In the preferred embodiment, the RF oscillator 60 operates at about 400 kHz, with any frequency from 300 kHz upwards into the HF range being feasible. The switched mode power supply typically operates at a frequency in the range of from 25 to 50 kHz. Coupled across the output lines 60C is a voltage threshold detector 68 having a first output 68A coupled to the switched mode power supply 66 and a second output 68B coupled to an "on" time control circuit 70. A micro-processor controller 72 coupled to the operator controls and display (shown in FIG. 1) is connected to a control input 66A of the power supply 66 for adjusting the generator output power by supply voltage variation and to a threshold-set input 68C of the voltage threshold detector 68 for setting peak RF output voltage limits.

In operation, the microprocessor controller 72 causes power to be applied to the switched mode power supply 66 when electrosurgical power is demanded by the surgeon operating an activation switch arrangement which may be provided on a hand-piece or footswitch (see FIG. 1). A constant output voltage threshold is set independently of the supply voltage via input 68C according to control settings on the front panel of the generator (see FIG. 1). Typically, for desiccation or coagulation the threshold is set at a desiccation threshold value between 150 volts and 200 volts. When a cutting or vaporisation output is required the threshold is set to a value in the range of from 250 or 300 volts to 600 volts. These voltage values are peak values. Their being peak values means that for desiccation at least it is preferable to have an output RF waveform of low crest factor to give maximum power before the voltage is clamped at the values given. Typically a crest factor of 1.5 or less is achieved.

When the generator is first activated, the status of the control input 601 of the RF oscillator 60 (which is connected to the "on" time control circuit 70) is "on", such that the power switching device which forms the oscillating element of the oscillator 60 is switched on for a maximum conduction period during each RF oscillation cycle. The power delivered to the tissue depends partly on the supply voltage applied to the RF oscillator 60 from the switched mode power supply 66 and partly on the tissue impedance. The voltage threshold for a desiccation output is set to cause trigger signals to be sent to the "on" time control circuit 70 and to the switched mode power supply 66 when the voltage threshold is reached. The "on" time control circuit 70 has the effect of virtually instantaneously reducing the "on" time of the RF oscillator-switching device. Simultaneously, the switched mode power supply is disabled so that the voltage supplied to oscillator 60 begins to fall. The operation of the generator in this way is described in detail in our European Patent Application No. 0754437, the disclosure of which is hereby incorporated by way of reference.

Figure 6A:
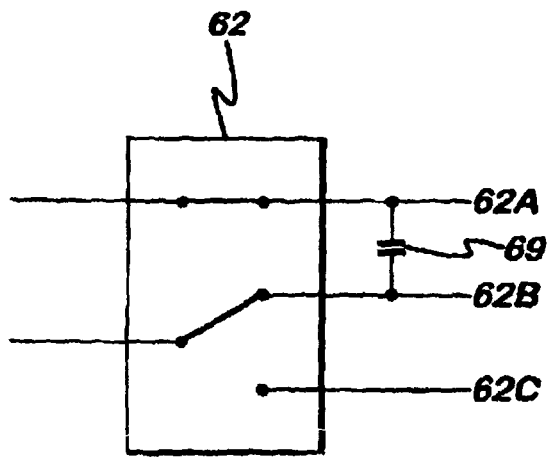

Output connections 62A, 62B and 62C from the generator 100 are thereby electrically connected to the jaw members 13 and 14, and to the cutting electrode 16 respectively. When it is desired to operate the instrument 102 in a coagulation mode, the controller 72 sets the switching circuit 62 to its "coag" state, as illustrated in FIG. 6A. In this set-up, the power signals from the oscillator are connected between output connections 62A and 62C. This means that the RF power signal is applied between the two jaw members 13 & 14. At the same time the controller sends a signal to the voltage threshold detector 68 to set the peak output voltage limit to a relatively lower "coagulating" level, as more particularly described in EP 0754437. In "coag" mode, the output from the generator is a relatively lower voltage, with a corresponding relatively higher current.

Figure 6B:
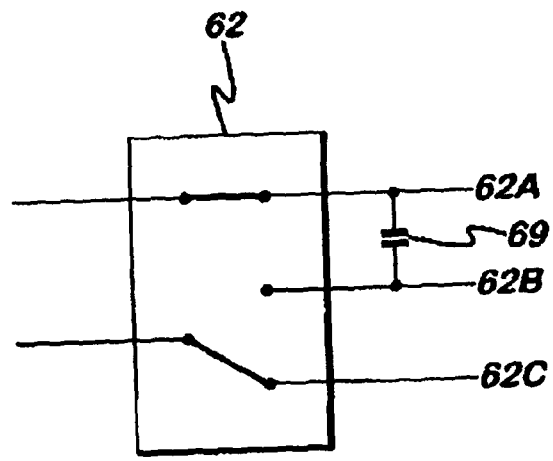

Alternatively, when it is desired to operate the instrument 102 in a cutting mode, the controller 72 sets the switching circuit 62 its "cut" position. This is illustrated in FIG. 6B, in which the signals from the oscillator 60 are connected between output connections 62A and 62B. This means that the RF power signal is applied between the cutting electrode 16 and the jaw members 13 & 14. At the same time as the controller 72 sets the switching circuit to the position in FIG. 6A, it also sends a signal via line 68C to the voltage threshold detector 68 to set the peak output voltage limit to a relatively high "cutting" level. The control of this cutting signal is also described in more detail in EP 0754437, referred to earlier.

Figure 7:
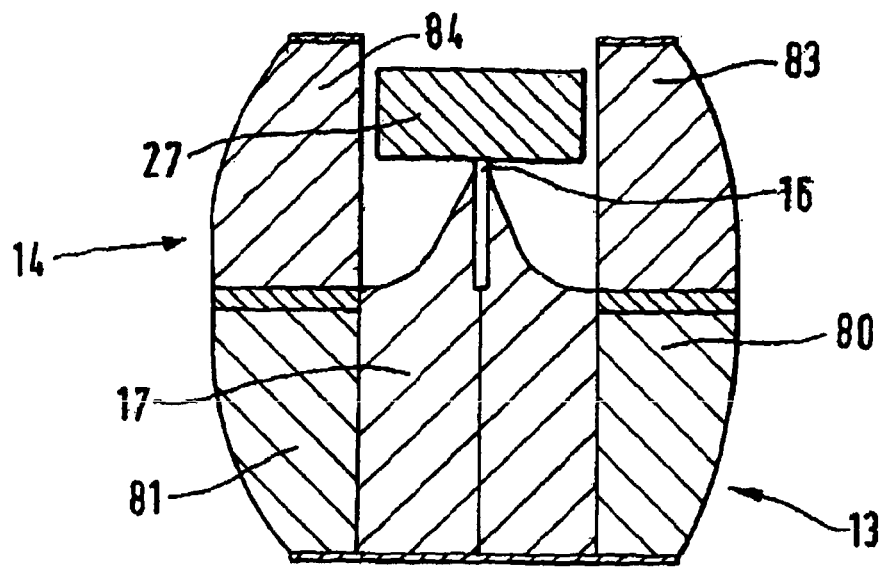
FIGS. 7 to 12 are schematic sectional diagrams of the end effector assembly of the instrument of FIG. 2, in different stages of operation.

The operation of the cutting forceps instrument will now be described, with reference to FIGS. 7 to 12, which are schematic diagrams showing the simplified movement of the various key components. FIG. 7 shows the jaws in their rest position, closed but with no tissue grasped between the jaws. The cutting electrode 16 pushes the anvil 27 upwardly against the support member (not shown in FIGS. 7 to 12).

Figure 8:
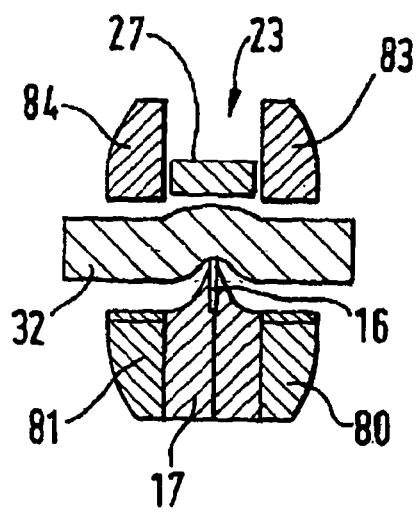
Figure 9:
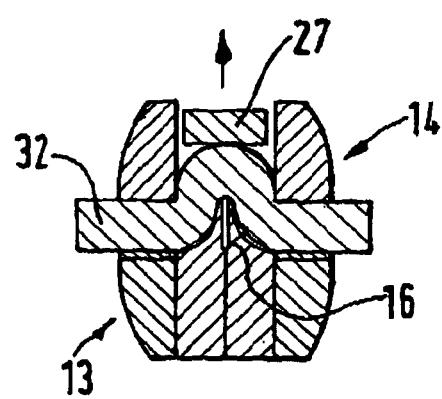
Figure 10:
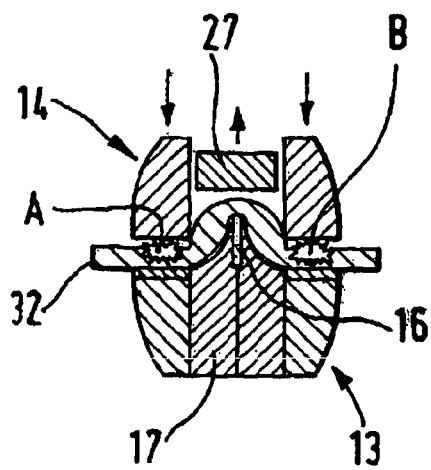

FIG. 8 shows the jaw members in their open position, with tissue 32 therebetween. With the jaws in the open position, the anvil 27 is no longer pushed upwardly by the cutting electrode 16, and consequently assumes a position more level with the base of the jaw member 14. The jaws are then closed as shown in FIGS. 9 & 10, such that the tissue 32 is squeezed between the jaw members 13 and 14. The anvil 27 is pushed upwardly by the tissue against the spring action of the support member, so as not to exert so great a force on the tissue as to squeeze the tissue against the cutting electrode as is supplied between the tissue-contacting members of the jaw members 13 and 14. Typically, the pressure exerted on the tissue by the tissue-contacting members of the jaw members 13 and 14 in the sealing areas A & B as depicted in FIG. 10 is between 0.5 and 1.0 MPa.

Figure 11:
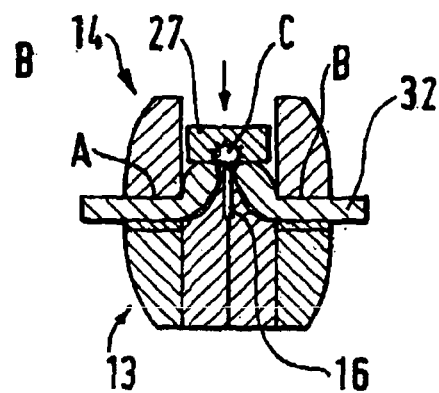
Figure 12:
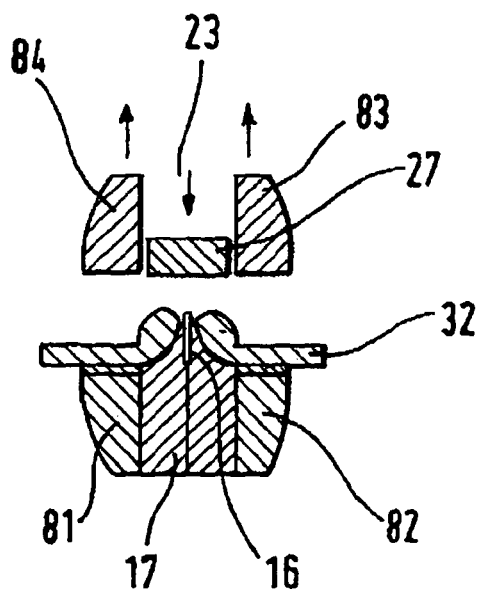

When the jaws have been fully closed, the electrosurgical generator 100 is actuated to supply an initial coagulating RF signal between jaw members 13 and 14 for a predetermined period of a couple of seconds up to several seconds, for example 1.5 to 4 seconds. This partially coagulates the tissue 32 in the sealing areas A & B. After a couple or several seconds, the coagulating RF signal is discontinued, and replaced by a cutting RF signal supplied between the cutting electrode 16 and the jaw members 13 and 14. This is shown in FIG. 11, during which time the spring movement of the anvil 27 exerts a force against the tissue of typically between 0.08 and 0.25 N/mm. The cutting electrode 16 electrosurgically severs the tissue 32 in the cutting area C as shown in FIG. 11, the cutting area C lying between the sealing areas A & B. The cutting signal is discontinued after a predetermined time, typically 2 to 3 seconds (although time periods up to about 5 seconds or as small as 1.5 seconds are acceptable), and is automatically replaced by the coagulating RF signal as previously described. This re-application of the RF coagulating signal takes place typically for a couple of seconds (although time periods between about 1.5 and about 6 seconds may be used) before the jaws are re-opened as shown in FIG. 12 to release the severed tissue.

The spring-loading of the anvil 27 allows for a differential force to be applied to the tissue 32 at the sealing areas A & B as compared to the cutting area C. This allows for a sufficient force to be applied to the sealing areas to ensure effective sealing, without the same force being applied between the anvil 27 and the cutting electrode 16. Thus, there is much less likelihood of problems being encountered where the force exerted between the anvil and the cutting electrode is sufficient to cause a mechanical cutting of the tissue 32 before the electrosurgical cutting signal is supplied to the tissue. In addition, the spring loading of the anvil allows the device to adapt to any tissue shrinkage caused by the coagulation of the tissue. If shrinkage occurs, the spring-loaded anvil ensures that a controlled force is still applied against the cutting electrode 16.

Although the forceps device described herein is shown as an endoscopic instrument, the invention can also be employed in connection with open instruments, as is described in published US patent application 2009/0234355. Other modifications, both as to the equipment and operating procedures, can be accomplished without departing from the scope of the invention. For example, the initial RF coagulating waveform can be initiated by activating the pedal 106A, while activation of the pedal 106B causes the controller 72 to supply the RF cutting waveform which is then automatically followed by the re-application of the RF coagulating waveform. Alternatively, a single activation of the pedal 106B can cause the controller 72 to initiate a three-stage process, namely the RF coagulating waveform, followed automatically by the RF cutting waveform, followed automatically by the re-application of the RF coagulating waveform. Furthermore, while the RF coagulating waveform is typically a "pure" coagulating waveform, the RF cutting waveform can either be a "pure" RF cutting waveform or alternatively a blended waveform of a combination as described in U.S. Pat. Nos. 6,966,907 and 7,344,532. In this way, the "cutting" waveform actually comprises a blended signal consisting of a rapidly alternating application of the cutting and coagulating waveforms. Whether "pure" or "blended", the cutting waveform is followed by a re-application of the RF coagulating waveform. In this way, the initial RF coagulating waveform does not need to be applied for such a period of time that the tissue is fully coagulated prior to cutting, leaving sufficient moisture within the tissue for the RF cutting waveform to be effective.

The invention claimed is:

1. An electrosurgical generator for generating radio frequency power, the electrosurgical generator comprising:
   a radio frequency output stage having a plurality of output connections;
   one or more sources of radio frequency output power coupled to the output stage;
   a controller configured to: (i) cause a supply of a first coagulating RF waveform to the output connections and a second cutting RF waveform to the output connections, and (ii) transmit at least one of the first coagulating RF waveform and the second cutting RF waveform to the output connections; and
   in response to a first activation signal from a user, the controller supplies the second cutting RF waveform for a first period of time required to perform an electrosurgical cut of tissue, followed automatically by the first coagulating RF waveform for a second period of time required to complete coagulation of the cut tissue, wherein the controller supplies: (1) the second cutting RF waveform for the first period of time, and (2) the first coagulating RF waveform for the second period of time, in order, once per activation signal.

2. The generator according to claim 1, wherein the controller is configured to supply the first coagulating RF waveform for a coagulation time period required to partially coagulate the tissue to be cut prior to the supply of the second cutting RF waveform for the first period of time.

3. The generator according to claim 2, wherein the supply of the first coagulating RF waveform for the coagulation time period is in response to the first activation signal.

4. The generator according to claim 2, wherein the supply of the first coagulating RF waveform for the coagulation time period is in response to an initial activation received at the controller prior to the first activation signal.

5. The generator according to claim 1, wherein the second cutting RF waveform is a blended signal that rapidly alternates between a cutting RF waveform and a coagulation RF waveform.

* * * * *